United States Patent
Pang et al.

(10) Patent No.: US 11,602,498 B2
(45) Date of Patent: Mar. 14, 2023

(54) METHOD AND APPARATUS FOR OXIDIZER-FREE EYELASH PERMING

(71) Applicant: L'ORÉAL, Paris (FR)

(72) Inventors: Christopher Pang, New York, NY (US); Kyoo Jin Park, Leonia, NJ (US)

(73) Assignee: L'OREAL, Paris (FR)

( * ) Notice: Subject to any disclaimer, the term of this patent is extended or adjusted under 35 U.S.C. 154(b) by 281 days.

(21) Appl. No.: 17/007,466

(22) Filed: Aug. 31, 2020

(65) Prior Publication Data

US 2022/0062153 A1   Mar. 3, 2022

(51) Int. Cl.
*A61Q 5/06* (2006.01)
*A61K 8/81* (2006.01)
*A45D 2/48* (2006.01)

(52) U.S. Cl.
CPC .............. *A61K 8/8182* (2013.01); *A45D 2/48* (2013.01); *A61Q 5/06* (2013.01); *A61K 2800/30* (2013.01)

(58) Field of Classification Search
CPC . A61Q 5/06; A61Q 1/10; A61Q 5/065; A61K 8/8182; A61K 2800/30; A45D 2/48
USPC ......................................... 424/70.7; 132/216
See application file for complete search history.

(56) References Cited

U.S. PATENT DOCUMENTS

| 7,179,302 | B2 | 2/2007 | Boswell et al. | |
| 7,938,128 | B2* | 5/2011 | Gueret | A45D 40/26 132/218 |
| 10,507,175 | B1* | 12/2019 | Lee | A61K 8/8152 |
| 2005/0166939 | A1* | 8/2005 | Stroud | A45D 40/30 132/216 |
| 2011/0150807 | A1* | 6/2011 | Bui | A61K 8/925 424/70.7 |
| 2013/0039874 | A1* | 2/2013 | Li | A61K 8/8152 424/70.7 |
| 2019/0001163 | A1* | 1/2019 | Rughani | A61Q 5/065 |

FOREIGN PATENT DOCUMENTS

| EP | 1028701 B1 | 7/2005 |
| KR | 101823401 B1 | 2/2018 |
| WO | 2005072688 A1 | 10/2004 |
| WO | 2002071890 A1 | 9/2020 |

OTHER PUBLICATIONS

French Search report and Written Opinion for corresponding FR Application No. 2010130, dated Jun. 17, 2021.
Mintel Record ID: 5670139.
Mintel Record ID: 3846661.
Database WPI, Week 201812, Thomson Scientific, London GB, XP002803364, Feb. 1, 2018.

* cited by examiner

*Primary Examiner* — Eisa B Elhilo
(74) *Attorney, Agent, or Firm* — Meagher Emanuel Laks Goldberg & Liao, LLP

(57) ABSTRACT

Disclosed is an oxidizer-free method for providing semi-permanent curl to eyelashes, and a kit for use with the method. The method involves a three-step process: (i) applying a first composition that includes a reducing agent to an eyelash, (ii) applying a second composition that includes a contractile polymer to the eyelash, and (iii) manually lifting the eyelash. Unlike conventional lash lifting techniques, the disclosed method requires no glue, silicone pads, compositions with oxidizing agents, or heating.

20 Claims, 1 Drawing Sheet

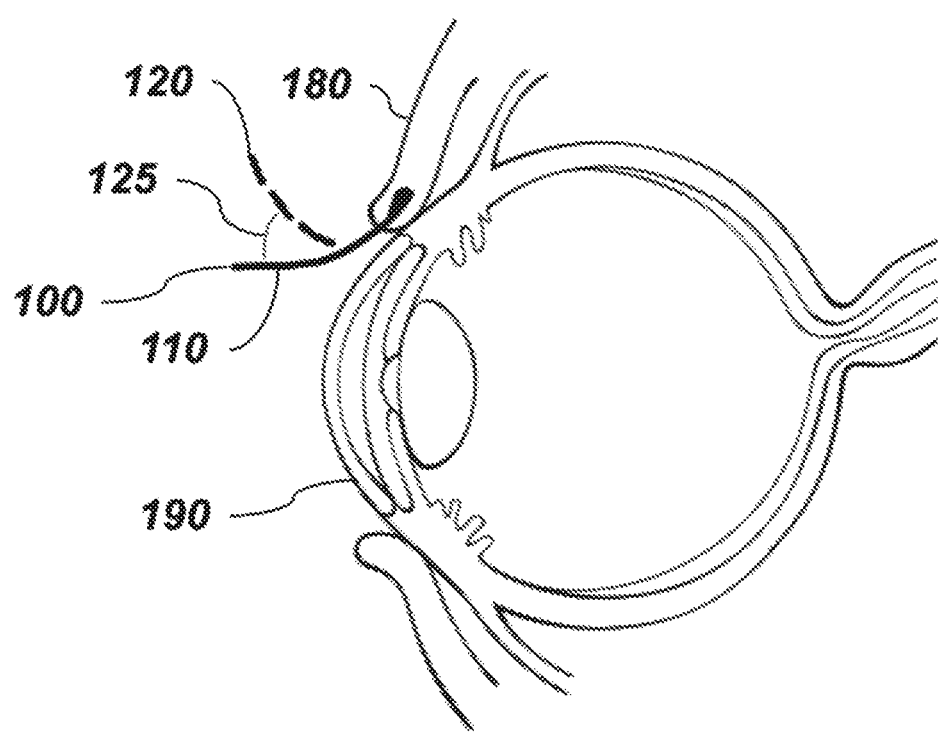

METHOD AND APPARATUS FOR OXIDIZER-FREE EYELASH PERMING

FIELD OF THE INVENTION

The present invention relates to eyelash perming, and specifically to an oxidizer-free method and apparatus for semi-permanent eyelash perming.

BACKGROUND

In beauty salons, eyelashes may sometimes be treated to provide long-lasting additional lift or curl. This is currently done via a costly eyelash "perm". A traditional "perm" process involves three steps—(1) applying a reducing agent, (2) separating the lashes or mechanically curling the lashes with a roller or mold, and (3) applying an oxidizing agent, and potentially applying air and heat, to lock the lashes into a desired shape.

Unfortunately, oxidizers are not safe to use around the eyes. As such, removing the oxidizer step is desirable. However, previous attempts to eliminate oxidizers have failed to provide long-lasting lift or curl—existing product solutions often lose list within a few hours.

As such, an inexpensive, oxidizer-free eyelash perming method and apparatus that provides long-lasting lift or curl is needed.

BRIEF SUMMARY

The present invention is directed to an oxidizer-free method for providing semi-permanent curl to eyelashes. The method involves a three-step process: (i) applying a first composition that includes a reducing agent to an eyelash, (ii) applying a second composition that includes a contractile polymer to the eyelash, and (iii) manually lifting the eyelash. The method requires no glue or silicone pads. Optionally, the first composition may be allowed to sit on the eyelash for between 2 and 40 minutes before applying the second composition. Optionally, the two compositions are applied to both a top and bottom eyelash. Optionally, the top eyelash is separated from the bottom eyelash prior to applying the first composition and the second composition. Optionally, the method also includes removing the first composition prior to applying the second composition.

Optionally, the method then involves applying a pigmented composition over the second composition.

Optionally, the method includes repeating the application process every 1-3 months.

Optionally, the contractile polymer is a film-forming polymer comprising at least one cyclic group selected from the group consisting of cyclic amides, cyclic amines, and mixtures thereof. Optionally, the cyclic amide group and/or cyclic amine group of the at least one film forming polymer comprise one or more aromatic or aliphatic ring structures. Optionally, the second composition further comprises water. Optionally, the second composition includes at least one film forming polymer in addition to the contractile polymer.

Optionally, the first composition and second composition are free of colorants.

A second aspect of the present disclosure is drawn to an oxidizer-free kit for providing semi-permanent curl to eyelashes. The kit includes (i) a first composition that has a reducing agent, (ii) a second composition that has a contractile polymer, and (iii) an applicator, eyelash separator, or both.

BRIEF DESCRIPTION OF THE DRAWINGS

FIG. 1 is an illustration of an eye and an upper eyelash.

DETAILED DESCRIPTION

As used herein, articles such as "a" and "an" when used in a claim, are understood to mean one or more of what is claimed or described.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the term "at least one" means one or more and thus includes individual components as well as mixtures/combinations.

As used herein, the term "free [of an ingredient]" means that the identified ingredient is only present in an amount below its detectable limit, and preferably that the composition contains 0% of the identified ingredient.

As used herein, the terms "include", "includes" and "including" are meant to be non-limiting.

As used herein, the term "substantially free [of an ingredient]" means that the composition contains less than 1% of the identified ingredient.

The present invention is directed to an oxidizer-free method for providing semi-permanent curl to eyelashes, allowing the method to be used safely near the eyes. The method comprises, consists essentially of, or consists of three steps: (i) applying a first composition that includes a reducing agent to an eyelash, (ii) applying a second composition that includes a contractile polymer to the eyelash, and (iii) manually lifting the eyelash.

Applying the First Composition

The first step of the method is to apply a first composition that comprises a reducing agent to at least one eyelash. The first composition may optionally be applied via an applicator. The first composition may be applied to a top eyelash, a bottom eyelash, or both. The top eyelashes may be separated from the bottom eyelash prior to applying the composition, optionally using an eyelash separator.

First Composition

The first composition must include a reducing agent. Reducing agents include, but are not limited to, thiols, borohydrides, or their derivatives. Thiols may include, for example, thiolactic acid, the salts of these thiols, phosphines, bisulphite, sulphites, thioglycolic acid, and also its esters, particularly glycerol monothioglycolate, and thioglycerol. A preferred embodiment utilizes ammonium thioglycolate. Borohydrides may include, for example, borohydride, cyanoborohydride, triacetoxyborohydride and trimethoxyborohydride salts: sodium, lithium, potassium, calcium, quaternary ammonium (tetramethylammonium, tetraethylammonium, tetra-n-butylammonium and benzyltriethylammonium) salts; and catecholborane.

The reducing agent is generally present in the first composition in an amount of between 0.01 and 20% by weight of the first composition.

The first composition can be in any form such as, for example, an anhydrous composition, an oil-in-water (O/W) emulsion including a silicone-in-water emulsion, a water-in-oil (W/O) emulsion including a water-in-silicone emulsion, a multiple emulsion, etc.

In preferred embodiments, the first composition may be a solution, comprising the reducing agent, a pH adjuster, and a solvent. For example, in some embodiments, the first composition may include the reducing agent, sodium hydroxide, and water.

In some embodiments, the first composition is substantially free of colorants. In some embodiments, the first composition is free of colorants.

In practice, a sufficient amount of the first composition will be used to allow the lashes to become susceptible to physical shaping.

Optionally, the first composition may be allowed to sit on the eyelash for between 2 and 40 minutes before applying a second composition, and preferably less than 30 minutes, more preferably less than 20 minutes, and more preferably between about 5 minutes and about 10 minutes.

Optionally, the method also includes removing at least some of the first composition, after the first composition has been allowed to sit on the eyelash, prior to applying a second composition. This may be done via any appropriate method, including, e.g., wiping, blotting, etc. In a preferred method, the first composition is removed via wiping with a tissue, towel, or other absorbent cloth.

Applying the Second Composition

After the first composition is applied, and after any optional delay and/or removal, the method requires applying a second composition to the eyelash, the second composition comprising a contractile polymer. The second composition may optionally be applied via an applicator. The second composition will be applied to the same eyelash or eyelashes that the first composition was applied to. The top eyelashes may be separated from the bottom eyelash prior to applying the composition, optionally using an eyelash separator.

Preferably, the second composition is applied to the underside of the eyelash. Referring briefly to FIG. 1, which shows a side view of an upper eyelash in its default position 100, connected to an upper eyelid 180, that is partially in front of an eye 190. For the upper eyelash, the second composition is preferably applied (e.g., via an applicator or brush tool) to the underside 110 of the eyelash 100, which is the side closest to the eye 190.

Second Composition

According to certain embodiments, the second composition comprises at least one contractile polymer. A contractile polymer is a polymer contracts and hardens when it dries. Some film-forming polymers are contractile polymers.

The glass transition temperature of the contractile polymer should be greater than or equal to 45° C. In some embodiments, $T_g$ is ≥80° C., ≥117° C., ≥125° C., and/or ≥200° C. The $T_g$ is preferably less than 400° C.

As $C_1$-$C_4$ monoalcohols (such as ethanol) can interfere with the film forming process, the second composition should avoid the use of such $C_1$-$C_4$ monoalcohols, and ethanol in particular. Other alcohols, such as glycols, are preferably only present at low levels (≤5% by weight relative to the contractile polymer)

Preferred copolymers that can function as contractile polymers do not contain a substantial majority of monomers that are water soluble, and preferably less than 60% of the monomers are water soluble. For copolymers that contains a pyrrolidone monomer (such as N-vinylpyrrolidone), less than 60% of the monomers should be the pyrrolidone monomer, and preferably less than about 50%.

Preferably, the contractile polymer contains at least some acrylate or acrylamide functionality. For example, copolymers that include methyacrylamide, acrylate copolymer, styrene/acrylates copolymers, and polyacrylates such as polyacrylate-22.

The contractile polymer may be one or more film-forming polymers comprising at least one cyclic group selected from the group consisting of cyclic amides, cyclic amines, and mixtures thereof. Preferably, the at least one film-forming polymer comprising at least one cyclic group selected from the group consisting of cyclic amides, cyclic amines, and mixtures thereof is non-ionic and water-soluble or water-dispersible. Without wishing to be bound by theory, it is believed that the presence of a sufficient amount of the at least one film forming polymer comprising at least one cyclic group selected from the group consisting of cyclic amides, cyclic amines, and mixtures thereof in the compositions of the present invention results in a curling effect on hair, eyebrows and/or eyelashes after application to the hair, eyebrows and/or eyelashes (and after the applied composition has dried).

According to preferred embodiments, the film forming polymer comprising at least one cyclic group selected from the group consisting of cyclic amides, cyclic amines, and mixtures thereof has a weight average molecular weight in a range from about 10,000 daltons to about 1,000,000 daltons, preferably from about 20,000 daltons to about 800,000 daltons, preferably from about 50,000 daltons to about 600,000 daltons, and preferably from about 100,000 daltons to about 500,000 daltons, including all ranges and subranges therebetween such as, for example, 15,000 daltons to 900,000 daltons, 200,000 daltons to 400,000 daltons, 10,000 daltons to 150,000 daltons, etc.

Preferably, the cyclic amide group and/or cyclic amine group of the at least one film forming polymer comprise one or more aromatic or aliphatic ring structures. Preferably, the rings have a size of from 4 to 10 ring members, preferably 5 to 8 ring members, and preferably 5 to 6 ring members, including all ranges and subranges therebetween.

Preferably, the cyclic amide group and/or cyclic amine group of the at least one film forming polymer are polymerizable ethylenically unsaturated monomers having a cyclic amine residue or a cyclic amide residue. Accordingly, the cyclic amide groups or monomers of the film-forming polymers useful in the present invention may include cyclic amide residues that are, or include, heterocyclic ring structures such as lactams and the like such as, for example, α-Lactam, β-lactam, γ-lactam, δ-lactam, and ε-lactam. Preferably, the cyclic amide is a pyrrolidone (a γ-lactam) a caprolactam, or combinations thereof.

Preferred cyclic amine groups include various heterocyclic amines such as, for example, azoles, pyrroles, pyrrolidines, carbamates, and the like. Preferably, the cyclic amine group is an imidazole.

Optionally, the film forming polymer comprising at least one cyclic group selected from the group consisting of cyclic amides, cyclic amines, and mixtures thereof may further comprise other groups in addition to the cyclide amide groups and/or cyclic amine groups.

If present, the additional group(s) are preferably acrylamide monomer(s), preferably having one or more —$C_3H_5NO$ functional groups. Specific examples of such additional groups include, but are not limited to, (meth) acrylamides.

An example of a preferred film forming polymer comprising at least one cyclic group selected from the group consisting of cyclic amides, cyclic amines, and mixtures thereof is LUVISET® CLEAR AT3, a copolymer of N-vinyl pyrrolidone, methacrylamide, and N-vinylimidazole commercially available from BASF of Ludwigshafen, Germany.

Preferably, the film forming polymer comprising at least one cyclic group selected from the group consisting of cyclic amides, cyclic amines, and mixtures thereof is present in an amount ranging from about 1% to about 40% by weight, preferably from about 3% to about 35% by weight, preferably from about 5% to about 30% by weight, and preferably from about 7% to about 25% by weight, all weights being based on the total weight of the composition, including all ranges and subranges therebetween. Preferably, the compositions of the present invention contain 7% or more by weight of the film forming polymer comprising at least one cyclic group selected from the group consisting of cyclic amides, cyclic amines, and mixtures thereof, preferably 10% or more by weight, preferably 15% or more by weight, all weights being based on the weight of the composition.

Optionally, embodiments of the second composition may further comprise at least one additional film forming agent in addition to the film forming polymer comprising at least one cyclic group selected from the group consisting of cyclic amides, cyclic amines, and mixtures thereof other groups in addition to the cyclic amide groups and/or cyclic amine groups.

If present, the at least one additional film forming agent may be any other film forming agent suitable for use in a composition for application to hair, eyebrows and/or eyelashes.

For example, the at least one additional film forming agent may include at least one cyclic amide monomer (hereinafter "second cyclic amide monomer"). The fraction (e.g., weight fraction) of the second cyclic amide monomer in the at least one additional film forming polymer is at least about 70%, preferably at least about 75%, and preferably at least about 80%. Further, the second cyclic amide monomer is preferably selected from a vinyl pyrrolidone (a γ-lactam) a caprolactam, and combinations thereof.

Suitable examples of the additional film forming agent include, but are not limited to, vinyl pyrrolidone/vinyl acetate copolymers having at least 70% vinyl pyrrolidone monomer, such as LUVIKSOL 73E, LUVIKSOL 73W; polyvinylcaprolactam, such as LUVIKSOL Plus; and polyvinyl pyrrolidone homopolymer such as PVP K-60 (or PLASDONE K-60), PVPK-90 (or PLASDONE K-90), or PVP K-120 (or PLASDONE K-120), each commercially available from Ashland, Inc. of Kovington, Ky.

Specific examples also include, but are not limited to, a silicone polymer such as, for example, a non-ionic silicone copolymer such as a non-ionic dimethicone copolymer. The silicone polymer or copolymer may be in the form of particles dispersed in an aqueous dispersion medium. Non-limiting examples of non-ionic silicone polymers include polymethylsiloxane resin, a linear block copolymer, and a mixture thereof. More specifically, non-limiting examples include a dimethicone copolymer such as a copolymer of dimethylpolysiloxane and vinyl dimethylpolysiloxane (i.e., a polydimethylsiloxane/vinyl copolymer) or a copolymer of dimethylpolysiloxane and a (meth)acrylate, with the dimethicone copolymer optionally being crosslinked and/or end-capped with functional groups. For example, a polydimethylsiloxane and vinyl dimethylpolysiloxane may comprise dimethylpolysiloxane that is crosslinked with vinyl dimethylpolysiloxane and/or dimethylpolysiloxane that is end-capped with vinyl dimethylpolysiloxane. A preferred compound includes dimethylpolysiloxane crosslinked with vinyl dimethylpolysiloxane. An example of a particularly useful dimethicone copolymer is a divinyl-dimethicone/dimethicone copolymer available as DOWSIL HMW 2220 Non-Ionic Emulsion, available from Dow Corning of Midland, Mich. This is a 60 percent active aqueous dispersion of divinyldimethicone/dimethicone copolymer and comprising $C_{12}$-$C_{13}$ Pareth-3 and $C_{12}$-$C_{13}$ Pareth-23.

Specific examples further include non-crosslinked acrylate and acrylic co-polymers, urethane polymers, polyesters and combinations thereof. A non-limiting example of a suitable non-crosslinked additional film forming agent is sodium alginate, available as PROTANAL PH 6160 from FMC Health and Nutrition of Philadelphia, Pa.

Preferably, if present, the additional film forming agent is present in an amount ranging from about 0.1% to about 40% by weight, preferably from about 0.5% to about 30% by weight, preferably from about 1% to about 20% by weight, and preferably from about 2% to about 10% by weight, all weights being based on the total weight of the composition, including all ranges and subranges therebetween. Preferably, the compositions of the present invention contain 2% or less by weight of the additional film forming agent, preferably 1% or less by weight, preferably 0.5% or less by weight, all weights being based on the weight of the composition.

Preferably, the compositions of the present invention contain more film-forming polymer comprising at least one cyclic group selected from the group consisting of cyclic amides, cyclic amines, and mixtures thereof than additional film forming agent by weight. Preferably, the film-forming polymer comprising at least one cyclic group selected from the group consisting of cyclic amides, cyclic amines, and mixtures thereof constitutes at least 55% percent by weight of the film forming component of the compositions of the present invention, at least 60% by weight, at least 75% by weight, at least 80% by weight, and least 90% by weight, all weights being based on the total weight of the film forming component of the composition, with the remainder of the film forming component being made up of the additional film forming agent(s).

For example, the film-forming component may comprise from about 60% to about 95% by weight of a copolymer of N-vinyl pyrrolidone, methacrylamide, and N-vinylimidazole; from about 9% to about 25% by weight of a nonionic film-forming polymer having a fraction of a second cyclic amide monomer that is at least about 70% (e.g., a vinyl pyrrolidone/vinyl acetate copolymer or a polyvinylcaprolactam), and optionally from about 1% to about 3% by weight of a dimethicone copolymer.

Preferably, the combined contractile polymer/film forming components of the second compositions are present in an amount ranging from about 0.1% to about 40% by weight, preferably from about 0.5% to about 30% by weight, preferably from about 1% to about 25% by weight, and preferably from about 2% to about 20% by weight, all weights being based on the total weight of the composition, including all ranges and subranges therebetween. Preferably, the second compositions contain 40% or less by weight of the contractile polymer/film forming components, preferably 30% or less by weight, preferably 25% or less by weight, all weights being based on the weight of the composition.

The second compositions can be in any form such as, for example, an anhydrous composition, an oil-in-water (O/W) emulsion including a silicone-in-water emulsion, a water-in-oil (W/O) emulsion including a water-in-silicone emulsion, a multiple emulsion, etc.

In preferred embodiments, the second composition comprises water. Preferably, water is present in the second composition in an amount ranging from about 30% to about 90% by weight, preferably from about 40% to about 85% by weight, preferably from about 45% to about 80% by weight, and preferably from about 50% to about 75% by weight, all weights being based on the total weight of the composition, including all ranges and subranges therebetween.

In some embodiments, the second composition is substantially free of colorants. In some embodiments, the second composition is free of colorants.

Lifting the Lashes

After the second composition is applied, the lashes should be lifted. Preferably, this is done manually using a finger, an applicator, brush tool, or other appropriate tool as desirable and appropriate. For example, a mascara brush could be used to lift the lashes.

Referring to FIG. 1, the eyelash (here, the upper eyelash) in its default position 100 is "lifted" to a lifted position 120, the lifted position 120 being deviated at an angle 125 from the default position 100 (it's "unlifted" position). The default position is the position the eyelash would occupy if no treatments had been applied. The deviation is in the vertical direction. That is—it is only deviated up, or down.

Typically, for the upper eyelash, it is deviated vertically upwards, as illustrated in FIG. 1. In preferred embodiments, the angle is at least 45 degrees, more preferably at least 60 degrees, still more preferably at least 70 degrees, and even more preferably at least 90 degrees. The angle is typically no more than about 135 degrees, and preferably no more than about 100 degrees. In preferred embodiments, the angle is between about 70 degrees and about 90 degrees.

This lifting is typically done for a period of time of less than about 5 minutes, preferably for no more than about 2 minutes, and more preferably no more than about 1 minute.

Typically, the angle 125 will be reduced immediately after the manual lifting is terminated. In some embodiments the angle 125 of all lifted eyelashes immediately after the lifting process will be between 40% and 60% of the angle 125 during lifting. That is, an eyelash that was originally lifted at a deviation of about 90 degrees may have a deviation of only about 45 degrees immediately after lifting. The reduction in deviation angle 125 will depend on numerous factors, including which specific contractile polymer(s) the composition includes, reducing agent used, times, temperatures, etc.

Further, lashes lifted in the disclosed manner should retain at least 87.5% of the deviation angle 125 when exposed to 20 minutes at 32° C. with 60% relative humidity.

Optionally, the lift imparted to the lashes will last at least 12 hours. Optionally, this method is only repeated every 1-3 months.

The above-described method utilizes no heating and no oxidizers, in order lift lashes.

In some embodiments, a pigmented composition over the second composition once the lashes are lifted.

This third, colored composition may optionally be an emulsion. Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments may also be included, and may be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

Color additives, such as natural extracts, may also be appropriate in various embodiments. One such example is spirulina paltensis extract, although other extracts may also be appropriate.

A second aspect of the present disclosure is drawn to an oxidizer-free kit for providing semi-permanent curl to eyelashes. The kit comprises, consists essentially of, or consists of: (i) a first composition that has a reducing agent, (ii) a second composition that has a contractile polymer, and (iii) an applicator, eyelash separator, or both. The applicator and/or eyelash separator may be any appropriate applicator or eyelash separator. Optionally, the kit contains instructions for use.

Example Method

A first composition was created by using a 1M solution of ammonium thioglycolate, and adjusting pH to 8.5. A second composition, listed in Table 1, was created by mixing all of the ingredients together until homogenous. Three artificial eyelashes, held in place with a thin flat clamp, were tested. The first and third artificial eyelashes had the first composition applied using an applicator. After 10 minutes, the first composition was removed with a clean wipe. The second composition was then applied to the second and third eyelashes using a second applicator. Holding each clamp horizontally, the first, second, and third eyelashes were each then held in place, using a finger, at approximately a 90-degree angle (as measured with a protractor) for 5 minutes.

TABLE 1

| Disclosed Second Composition | |
|---|---|
| Material | % w/w |
| Contractile Polymer | 2-20% |
| Rheological Modifier | 5-15% |
| Water | qs |

Evaluations

After the above method was used, the eyelashes were evaluated at their initial lift angles, and then after being subjected to hot and humid conditions (60% RH, 32° C.), for 20 minutes and evaluated again. The evaluations were done by holding each clamp horizontally, and measuring the angles formed by the eyelashes with a protractor. The results are summarized in Table 2.

TABLE 2

| Summary of Evaluations | | | |
|---|---|---|---|
| Evaluation | Eyelash 1 (First Composition Only) | Eyelash 2 (Second Composition Only) | Eyelash 3 (First + Second Composition) |
| Initial Angle after Lift | 0-10° | 30-40° | 40-50° |
| Angle after 20 minutes at 60% RH/32° C. | 0° | 20-30° | 35-45° |

As can be seen, not only are the initial deviations of the lashes, following lift, for eyelash 3 were superior to the comparative eyelash treatments, but there is a surprising synergy in the resilience of the lashes, that can be seen in the performance under hot and humid conditions. Specifically, although a treatment using the first composition only (eyelash 1) has no lift following the conditioning, the combination of first and second compositions (eyelash 3) is at least 5-15 degrees more lift than just using the second composition alone (eyelash 2). This is a significant improvement, and indicates the disclosed treatment provides significantly longer-lasting lift.

Example 2—Different Contractile Polymers

For this example, the application of the first composition, waiting for 10 minutes, wiping off, applying the second composition, followed by lifting of the lashes at a 90-degree deviation for 5 minutes was used. The same First Composition from Example 1 was used, and the Second Composition from Example 1 but with different contractile polymers were tested. The results are shown in Table 3, below.

TABLE 3

Results Of Different Contractile Polymers

| Contractile Polymer Trade Name | Contractile Polymer INCI Name | $T_g$ | Initial Angle After Lift | Angle after 20 minutes at 60% RH/ 32° C. |
|---|---|---|---|---|
| Luviset Clear | VP/Methacrylamide/ Vinyl Imidazole Copolymer | 209 | 45-60 | 40-55 |
| Luviset Shape | Polyacrylate 22 | 125-135 | 30-50 | 30-50 |
| Luviflex Soft | Acrylate Copolymer | 117.74 | 30 | 30 |
| Luviskol VA 73E | VP/VA Copolymer (in Ethanol) | 115 | 0 | 0 |
| Luviskol VA 73W | VP/VA Copolymer | 110 | 15-30 | 10-30 |
| Aculyn 33A | Acrylate Copolymer | 90 | 30-40 | 30-40 |
| Syntran 5620 CG | Styrene/Acrylates/ Ammonium Methacrylate Copolymer | 45-55 | 30-40 | 30-40 |
| Syntran 5760 | Styrene/Acrylates/ Ammonium Methacrylate Copolymer | 13 | 10-20 | 10-20 |
| Baycusan C1004 | Polyurethane-35 | −50 | 10-30 | 10-30 |

Those skilled in the art will recognize or be able to ascertain using no more than routine experimentation, many equivalents to the specific embodiments of the invention described herein. Such equivalents are intended to be encompassed by the following claims.

What is claimed is:

1. An oxidizer-free method for providing semi-permanent curl to eyelashes, comprising:
   a. applying a first composition comprising a reducing agent to an eyelash;
   b. applying a second composition to a bottom part of the eyelash, the second composition comprising a contractile polymer; and
   c. lifting at least a portion of the eyelash at angle relative to its normal unlifted position.

2. The oxidizer-free method according to claim 1, wherein the at least a portion of the eyelash is held at an angle greater than 70 degrees relative to its normal unlifted position during the lifting step.

3. The oxidizer-free method according to claim 2, wherein the eyelash is held at the angle using a finger, brush tool, or applicator.

4. The oxidizer-free method according to claim 1, further comprising allowing the first composition to sit on the eyelash for a period of time prior to applying the second composition, wherein the period of time is between 2 minutes and 40 minutes.

5. The oxidizer-free method according to claim 1, wherein the first composition and second composition are applied to both a top and bottom eyelash.

6. The oxidizer-free method according to claim 5, wherein the top eyelash is separated from the bottom eyelash prior to applying the first composition and the second composition.

7. The oxidizer-free method according to claim 1, further comprising removing the first composition prior to applying the second composition.

8. The oxidizer-free method according to claim 1, further comprising applying a third composition comprising a pigment to over the second composition.

9. The oxidizer-free method according to claim 1, further comprising reapplying the first and second compositions after a period of time of between 1 month and 3 months.

10. The oxidizer-free method according to claim 1, wherein the contractile polymer is a film-forming polymer comprising at least one cyclic group selected from the group consisting of: cyclic amides, cyclic amines, and mixtures thereof.

11. The oxidizer-free method according to claim 10, wherein the cyclic amide group and/or cyclic amine group of the at least one film forming polymer comprise one or more aromatic or aliphatic ring structures.

12. The oxidizer-free method according to claim 1, wherein the second composition further comprises water.

13. The oxidizer-free method according to claim 1, wherein the second composition further comprises at least one film forming polymer in addition to the contractile polymer.

14. The oxidizer-free method according to claim 1, wherein the first composition and second composition are free of colorants.

15. The oxidizer-free method according to claim 1, wherein the contractile polymer has a glass transition temperature $T_g \geq 45°$ C.

16. The oxidizer-free method according to claim 1, wherein the second composition is substantially free of a $C_1$-$C_4$ monoalcohol.

17. The oxidizer-free method according to claim 1, wherein the contractile polymer is a copolymer comprising at least one pyrrolidone monomer.

18. The oxidizer-free method according to claim 17, wherein less than 60% of monomers in the copolymer are pyrrolidone monomers.

19. The oxidizer-free method according to claim 17, wherein the contractile polymer has at least some acrylate or acrylamide functionality.

20. An oxidizer-free kit for providing semi-permanent curl to eyelashes, comprising:
   a. a first composition comprising a reducing agent;
   b. a second composition comprising a contractile polymer; and
   c. at least one applicator, eyelash separator, or both.

* * * * *